United States Patent
Leiner

(10) Patent No.: US 8,727,969 B2
(45) Date of Patent: May 20, 2014

(54) ENDOSCOPE

(75) Inventor: Dennis C. Leiner, Cape Elizabeth, ME (US)

(73) Assignee: Lighthouse Imaging, LLC, Windham, ME (US)

( * ) Notice: Subject to any disclaimer, the term of this patent is extended or adjusted under 35 U.S.C. 154(b) by 793 days.

(21) Appl. No.: 12/187,246

(22) Filed: Aug. 6, 2008

(65) Prior Publication Data

US 2009/0043167 A1 Feb. 12, 2009

Related U.S. Application Data

(60) Provisional application No. 60/954,114, filed on Aug. 6, 2007.

(51) Int. Cl.
| | | |
|---|---|---|
| A61B 1/00 | (2006.01) | |
| A61B 1/04 | (2006.01) | |
| A61B 17/12 | (2006.01) | |
| A61B 18/22 | (2006.01) | |
| A61M 13/00 | (2006.01) | |
| A61B 1/12 | (2006.01) | |
| A61B 1/06 | (2006.01) | |
| A61M 25/00 | (2006.01) | |

(52) U.S. Cl.
CPC ........... *A61B 17/12104* (2013.01); *A61B 18/22* (2013.01); *A61B 1/00165* (2013.01); *A61B 1/00119* (2013.01); *A61M 13/003* (2013.01); *A61M 25/00* (2013.01)
USPC ............ 600/114; 600/129; 600/156; 600/182

(58) Field of Classification Search
CPC ............. A61B 17/12104; A61B 18/22; A61B 1/00165; A61B 1/00119; A61M 13/003; A61M 25/00

USPC ......... 600/114, 121–125, 129, 175, 176, 132, 600/136, 160, 172, 180, 108, 171, 177, 182, 600/104, 115–116, 120, 153, 156, 157, 158
See application file for complete search history.

(56) References Cited

U.S. PATENT DOCUMENTS

| | | | |
|---|---|---|---|
| 3,556,085 A * | 1/1971 | Takahashi | 600/129 |
| 3,961,621 A * | 6/1976 | Northeved | 600/566 |
| 3,993,079 A | 11/1976 | Henriques de Gatztanondo | |
| 4,157,216 A * | 6/1979 | Plummer | 396/17 |
| 4,254,762 A | 3/1981 | Yoon | |
| 4,269,192 A | 5/1981 | Matsuo | |
| 4,273,109 A * | 6/1981 | Enderby | 600/175 |
| 4,624,243 A * | 11/1986 | Lowery et al. | 600/136 |
| 4,938,205 A * | 7/1990 | Nudelman | 600/108 |
| 5,406,940 A | 4/1995 | Melzer et al. | |
| 5,421,821 A | 6/1995 | Janicki et al. | |
| 5,467,762 A | 11/1995 | Sauer et al. | |
| 5,471,553 A | 11/1995 | Teshima | |
| 5,678,550 A * | 10/1997 | Bassen et al. | 600/431 |
| 5,817,061 A * | 10/1998 | Goodwin et al. | 604/164.03 |
| 6,001,084 A | 12/1999 | Riek et al. | |
| 6,011,889 A * | 1/2000 | Daniel et al. | 385/117 |
| 6,193,692 B1 * | 2/2001 | Harris et al. | 604/164.02 |
| 6,387,043 B1 | 5/2002 | Yoon | |
| 2005/0054900 A1 * | 3/2005 | Mawn et al. | 600/156 |
| 2005/0288622 A1 * | 12/2005 | Albrecht et al. | 604/23 |

\* cited by examiner

*Primary Examiner* — Alireza Nia
(74) *Attorney, Agent, or Firm* — Dennis R. Haszko

(57) ABSTRACT

An endoscope includes an outer tube having a sharpened distal end and a retractable sleeve slidably disposed in the outer tube. An image conduit is attached to the distal end of the retractable sleeve for imaging any object in contact with the distal tip of the image conduit.

23 Claims, 5 Drawing Sheets

ENDOSCOPE

CROSS REFERENCES TO RELATED APPLICATIONS

This application claims the benefit of U.S. Provisional Patent Application No. 60/954,114, filed Aug. 6, 2007.

BACKGROUND OF THE INVENTION

This invention relates generally to devices and techniques for performing endoscopic surgery.

The use of endoscopes enables minimally invasive surgical procedures to be performed in normally closed body cavities, such as the abdominal cavity. (Endoscopy in the abdominal cavity is referred to as laparoscopy.) The abdominal cavity typically needs to be insufflated prior to performing a laparoscopic procedure to create space between the abdominal wall and organs and arteries in the abdominal cavity. This space permits the various surgical devices to be safely inserted and used. Many other body cavities similarly need to be insufflated to perform an endoscopic procedure.

Verres needles are well known to surgeons for producing an initial entry incision during laparoscopic surgery and injecting gas into the abdominal cavity to insufflate the cavity. A Verres needle generally includes a hollow tube having a sharpened tip and means for injecting insufflation gas through the tube. The first surgical device typically inserted after the Verres needle is the laparoscope. Means for visualizing the insertion of the laparoscope are well known and are manufactured by companies such as Ethicon and Covidien.

A problem inherent with conventional Verres needles is that it has been difficult to precisely control the location of the needle tip while making the initial incision. The positioning of the needle tip during the initial incision is critical because insufflation has not yet been performed at this point in the procedure meaning that the patient's arteries and organs are in close proximity to the inside wall of the body cavity. The procedure can be particularly dangerous to the patient because if the needle tip is inserted too deeply, there is a risk of puncturing an artery, such as the aorta, or an internal organ. On the other hand, the body cavity cannot be insufflated if the needle tip is not fully inserted thorough the inside wall and into the body cavity.

Various attempts have been made to overcome the difficulty of positioning the needle tip during the initial incision. For example, U.S. Pat. No. 4,254,762, issued Mar. 10, 1981 to Yoon, describes a system including an "endoscope means" 10 and a "trocar means" 38 encircling the endoscope means. The trocar means has a sharpened end for puncturing the wall of a body cavity. The endoscope means permits the surgeon to visually monitor the puncture of a body cavity. The endoscope means is also spring-biased in the trocar means. When the sharpened end of the trocar means pierces the wall of a body cavity, the spring bias drives the endoscope means into contact with an abutment on the trocar means, thereby providing an audible signal of the completion of the puncture. Yoon does not specifically describe an endoscope designed to image tissue in contact with the tip of the endoscope. Conventional endoscopes are typically designed to image objects removed from the tip of the endoscope.

SUMMARY OF THE INVENTION

One embodiment of the present invention includes an endoscope comprising an outer tube having a sharpened distal end and a retractable sleeve slidably disposed in the outer tube. An image conduit is attached to the distal end of the retractable sleeve for imaging any object in contact with the distal tip of the image conduit.

DETAILED DESCRIPTION OF THE INVENTION

Figure 1:
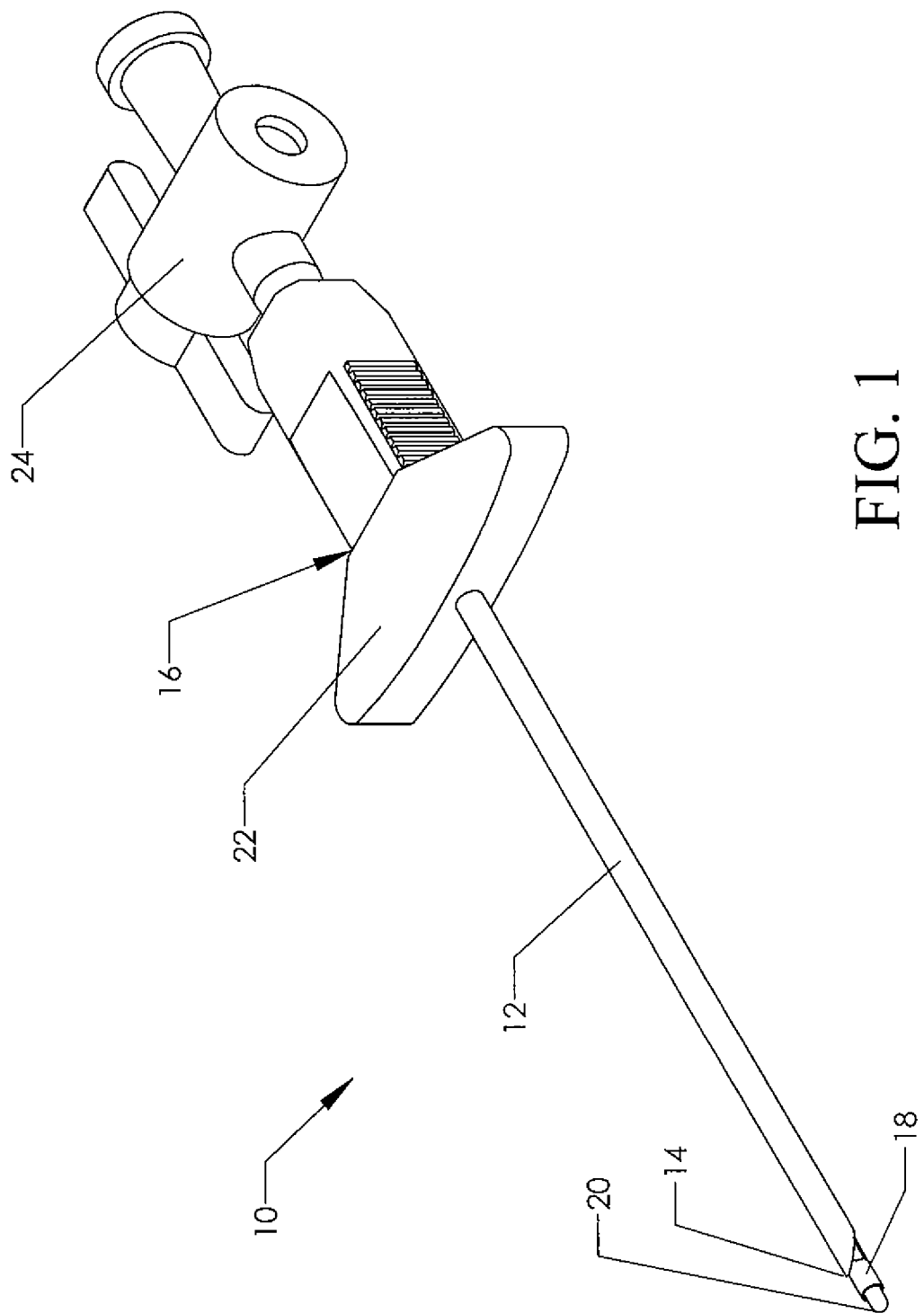
FIG. 1 is a perspective view of one embodiment of an endoscope.

Referring to the drawings wherein identical reference numerals denote the same elements throughout the various views, FIG. 1 shows one embodiment of an endoscope 10 that can be used for initiating laparoscopic surgery. The endoscope 10 includes means for making an initial incision in body tissue through which the device can be inserted into a body cavity. As used herein, the term "body cavity" refers to any space (typically fluid filled) in the body of a human or other animal. This includes, but is not limited to, the abdominal cavity, the thoracic cavity, and the subarachnoid space of the spinal column. In the illustrated embodiment, the endoscope 10 is an insufflation endoscope that includes means for insufflating the body cavity. The endoscope 10 also includes means for imaging anatomical regions in contact with the tip of the endoscope 10 (and thus in close proximity to the cutting means), thereby permitting safer initial entry into the body cavity. It should be noted that while the endoscope 10 is particularly useful in laparoscopic procedures, it is not so limited, and can be used in a variety of other procedures including lumbar punctures (e.g., spinal taps). It is also noted that as used herein, the term "proximal" refers to the end or portion of a structural element that is normally oriented or positioned outside of, or away from, the patient, while the term "distal" refers to the end or portion of a structural element that is normally oriented or positioned inside of, or nearest to, the patient.

The endoscope 10 includes an outer tube 12 having a sharpened distal end 14 and an end assembly 16 attached to the distal end thereof. A retractable sleeve 18 is slidably disposed in the outer tube 12; that is, the retractable sleeve 18 is coaxially situated inside the hollow interior of the outer tube 12 and is capable of sliding or moving longitudinally with respect to the outer tube 12. A shaped image conduit 20 is mounted to the distal end of the retractable sleeve 18. The end assembly 16 includes a handle portion 22 and a connector 24 for connecting the insufflation endoscope 10 to a source of insufflation gas. An optical system (not shown in FIG. 1, but described below) is connected to the end assembly 16 to enable viewing of the images produced by the insufflation endoscope 10.

Figure 2:
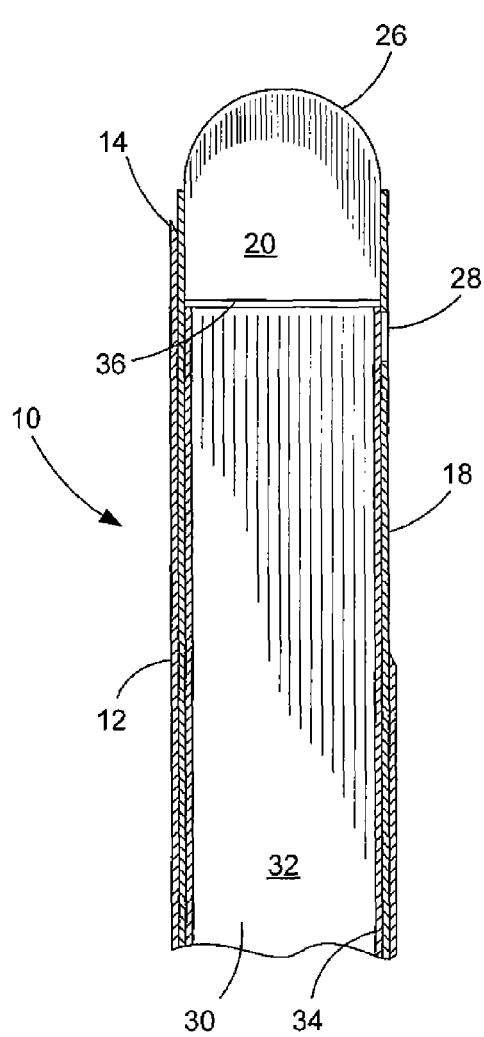
FIG. 2 is a cross-sectional view of the distal end of the endoscope of FIG. 1, with its retractable sleeve in an extended position.
Figure 3:
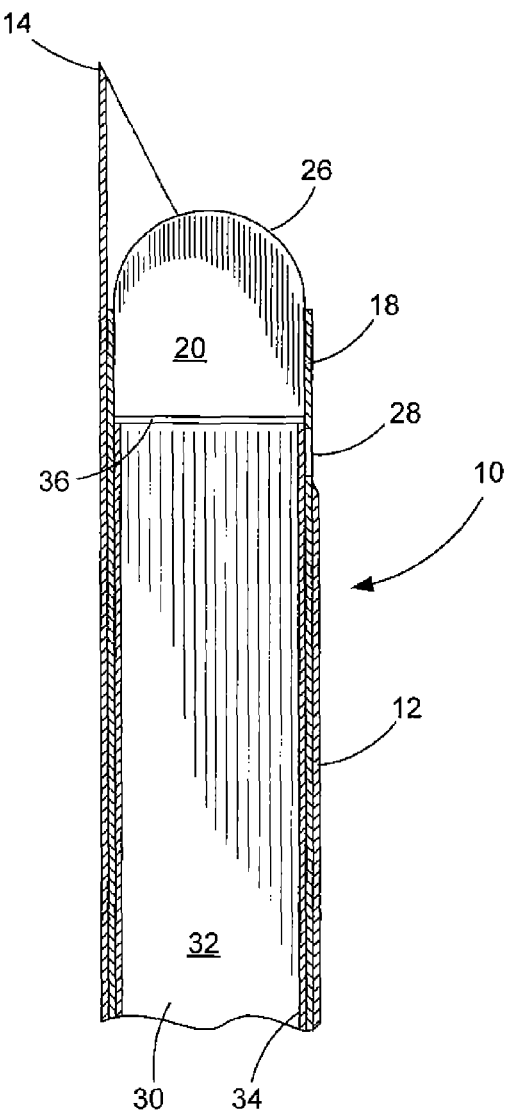
FIG. 3 is a cross-sectional view of the distal end of the endoscope of FIG. 1, with its retractable sleeve in a retracted position.

Referring to FIGS. 2 and 3, the sharpened distal end 14 of the outer tube 12 is configured into a pointed tip that is sufficiently sharp to make an incision through tissue and into a body cavity. The retractable sleeve 18 is a flat-ended tube having an open distal end. The image conduit 20 is fixed in the distal end of the retractable sleeve 18, with a portion of the image conduit 20 extending beyond the distal end of the retractable sleeve 18. This protruding portion defines a distal tip 26 of the image conduit 20. The retractable sleeve 18 is spring-loaded in such a manner that the distal end of the sleeve 18 is normally biased to protrude beyond the distal end 14 of the outer tube 12, as shown in FIG. 2. Thus, when the endoscope 10 is not in use, the sharpened distal end 14 is largely concealed to reduce the chance of the sharpened distal end 14 causing an injury. However, when the distal tip 26 is pressed against body tissue, the resulting force exerted thereon causes the retractable sleeve 18 to be retracted into the outer tube 12, as shown in FIG. 3. This exposes the sharpened distal end 14 to enable an incision to be made in the tissue. At least one insufflation channel 28 is formed through the sidewall of the retractable sleeve 18, adjacent to, but not overlapping, the image conduit 20.

The shaped image conduit 20 can be constructed from image fiber, available from several companies, such as Sumitomo Electric Industries, Ltd. and Fujikura America, Inc. Image fiber, which is well known for use in constructing fiberoptic endoscopes, generally comprises multiple optical fibers (typically made from silica, glass, plastic or the like) fused together with a one-to-one correspondence in their positions at the distal and proximal ends. The image conduit 20 transfers an image of an object in contact with the distal tip 26 to its proximal end. Any object in contact with the distal tip 26 will be in sharp focus. However, objects removed from the distal tip 26 generally will not be in sharp focus. The image conduit 20 does not function as a lens; it is not designed to image surfaces not in contact with the distal tip 26. In a conventional endoscope, this feature would be detrimental because it is normally desired to obtain a sharp image from objects removed from the tip of the endoscope. However, only the image at the distal tip 26 is of interest in the present invention. Because tissue is translucent or opaque, a conventional endoscope with a distal lens focusing on objects removed from the tip could not obtain a useful image.

In the illustrated embodiment, the image conduit 20 is shaped so that the distal tip 26 defines a rounded, blunt surface. This is similar to conventional Verres needles, so there is little difference in appearance. The surgeon is therefore able to use the insufflation endoscope 10 in the same manner as a conventional Verres needle, except the imaging means of the endoscope 10 allows the surgeon to visually monitor the cutting of the incision. The shaped image conduit 20 can have many other shapes as well. For example, the image conduit 20 could have a flat distal tip, which would likely be less expensive to manufacture, or the image conduit 20 could have a conical distal tip, which would be helpful in separating soft tissue when making the incision. Furthermore, the distal tip 26 could be sharpened, such as into a chisel shape, so as to form a cutting edge. This would eliminate any need for the outer tube 12 as a cutting implement.

An image guide 30 is removably mounted in the retractable sleeve 18 for transmitting the image formed at the proximal end of the shaped image conduit 20 to the proximal end of the endoscope 10. In one embodiment, the image guide 30 comprises a second image conduit 32 constructed from image fiber and enclosed in a protective sleeve 34. The protective sleeve 34 is open at both ends so that light can be transmitted through the length of the image guide 30. The distal end of the image guide 30 is positioned against the proximal end of the image conduit 20, and the image guide 30 extends through the remaining length of the retractable sleeve 18 such that its proximal end extends beyond the proximal end of the retractable sleeve 18. An index matching material 36 such as a gel or liquid is applied between the distal end of the image guide 30 and the proximal end of the image conduit 20 to reduce Fresnel reflections from these two surfaces.

Figure 4:
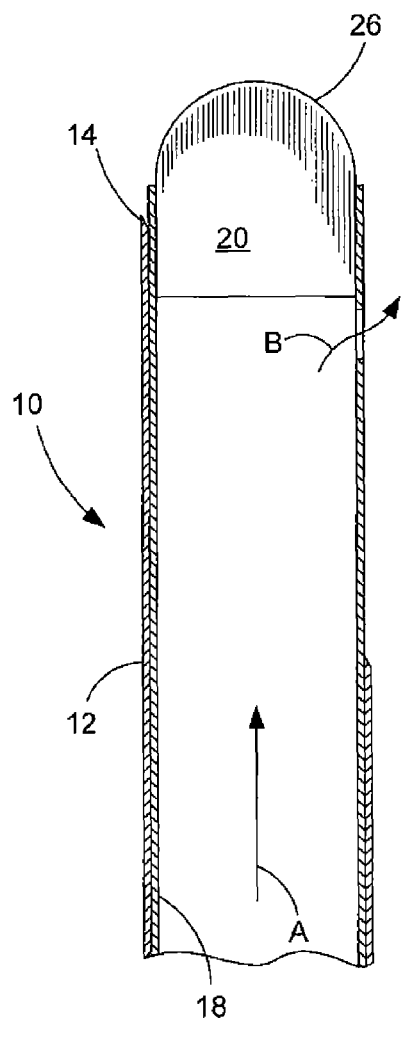
FIG. 4 is a cross-sectional view of the distal end of the endoscope of FIG. 1, with its image guide removed.

The image guide 30 is mounted in the retractable sleeve 18 in such a manner that permits it to be removed therefrom. For instance, the outer surface of the protective sleeve 34 can be such that the image guide 30 fits snugly inside the retractable sleeve 18, thereby producing a friction fit between these two components. Thus, the image guide 30 will generally be retained in the retractable sleeve 18 and thus move with the sleeve 18 when it slides within the outer tube 12. However, the image guide 30 can also be removed from the retractable sleeve 18 by pulling on its distal end. When the image guide 30 is removed, as shown in FIG. 4, the hollow interior of the retractable sleeve 18 is open. Thus, gas injected into the retractable sleeve 18 (depicted by arrow A) will flow out through the insufflation channel 28 (arrow B). Thus, insufflations of a body cavity can take place when the distal end of the endoscope 10 is positioned within the body cavity.

Figure 5:
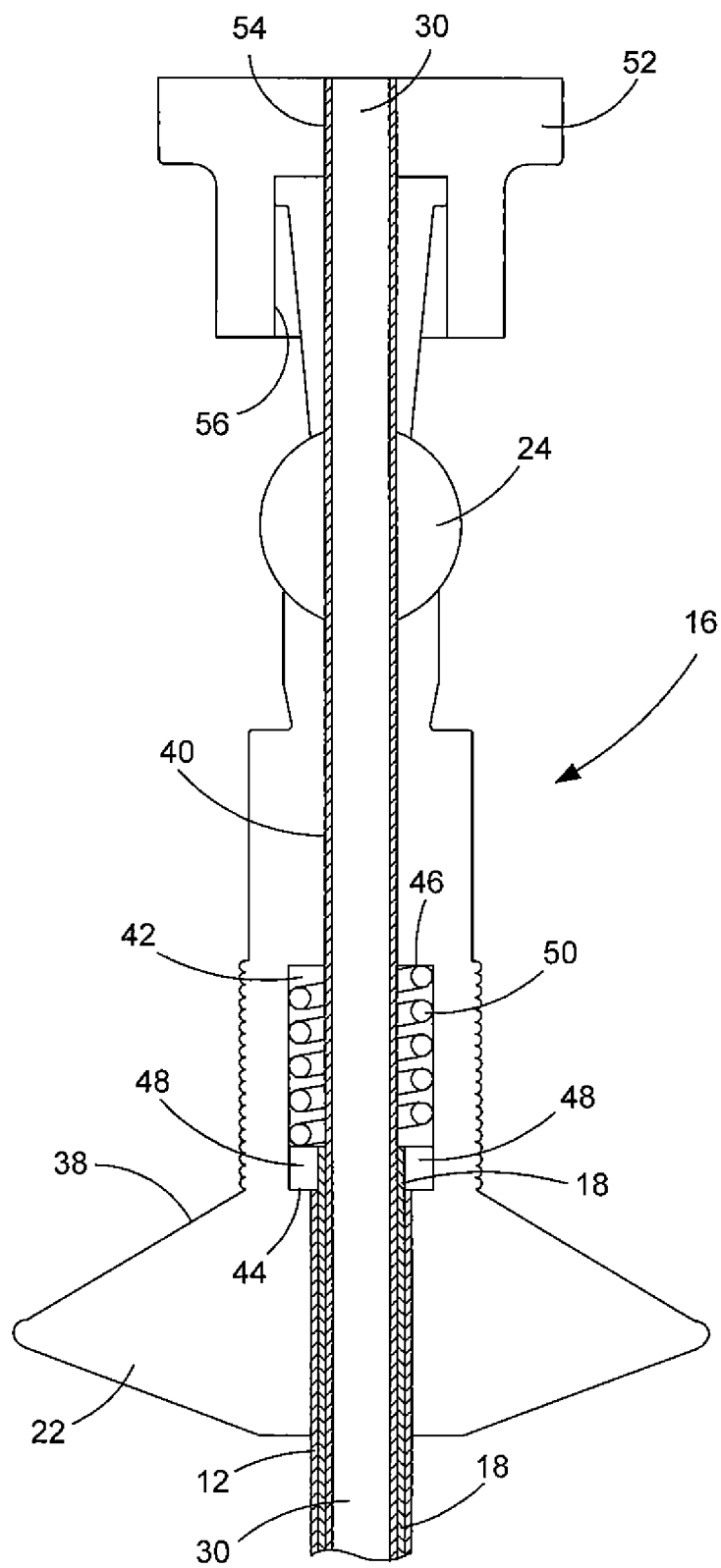
FIG. 5 is a cross-sectional view of an end assembly of the endoscope of FIG. 1.

Turning to FIG. 5, the end assembly 16 includes a body member 38 having a central through bore 40 formed therein. The handle portion 22 is integrally formed on the distal end of the body member 38, and the connector 24 is located between the handle portion 22 and the proximal end of the body member 38. The body member 38 is fixedly attached to the proximal end of the outer tube 12, which is located in the distal end of the bore 40. As mentioned above, the retractable sleeve 18 is spring-loaded within the outer tube 12. FIG. 5 shows one possible arrangement for this. The bore 40 includes an enlarged section 42 located intermediate the two ends of the bore 40. The distal end of the enlarged section 42, located adjacent to the proximal end of the outer tube 12, defines a distal shoulder or abutment 44, and the proximal end of the enlarged section 42 defines a proximal shoulder or abutment 46. The proximal end of the retractable sleeve 18 extends into the enlarged section 42. A ring 48 is formed on or fixed to the proximal end of the retractable sleeve 18 and is located in the enlarged section 42. The ring 48, which has substantially the same cross-sectional shape as the enlarged section 42, is capable of sliding within the enlarged section 42 as the retractable sleeve 18 moves back-and-forth within the outer tube 12. A compression spring 50 is located in the enlarged section 42, extending between the ring 48 and the proximal abutment 46. The spring 50 thus biases the ring 48 into engagement with the distal abutment 44, as shown in FIG. 5, which in turn biases the retractable sleeve 18 distally. A sufficient force exerted on the distal tip 26 will cause the retractable sleeve 18 and the ring 48 to move proximally, compressing the spring 50.

The image guide 30 extends through the bore 40 and beyond the proximal end of the body member 38. A knob 52 is fixed to the portion of the image guide 30 that extends beyond the proximal end of the body member 38. Specifically, the image guide proximal end is fixedly received within a central bore 54 formed in the knob 52. The bore 54 is open at the proximal end of the knob 52 so that the image guide 30 is able to optically interface with an optical system. A counter bore 56 formed in the distal end of the knob 52 fits snugly over the proximal end of the body member 38 so as to be removably retained thereon. The knob 52 and image guide 30 can be removed from the endoscope 10 by pulling on the knob 52 while grasping the handle portion 22.

Figure 6:
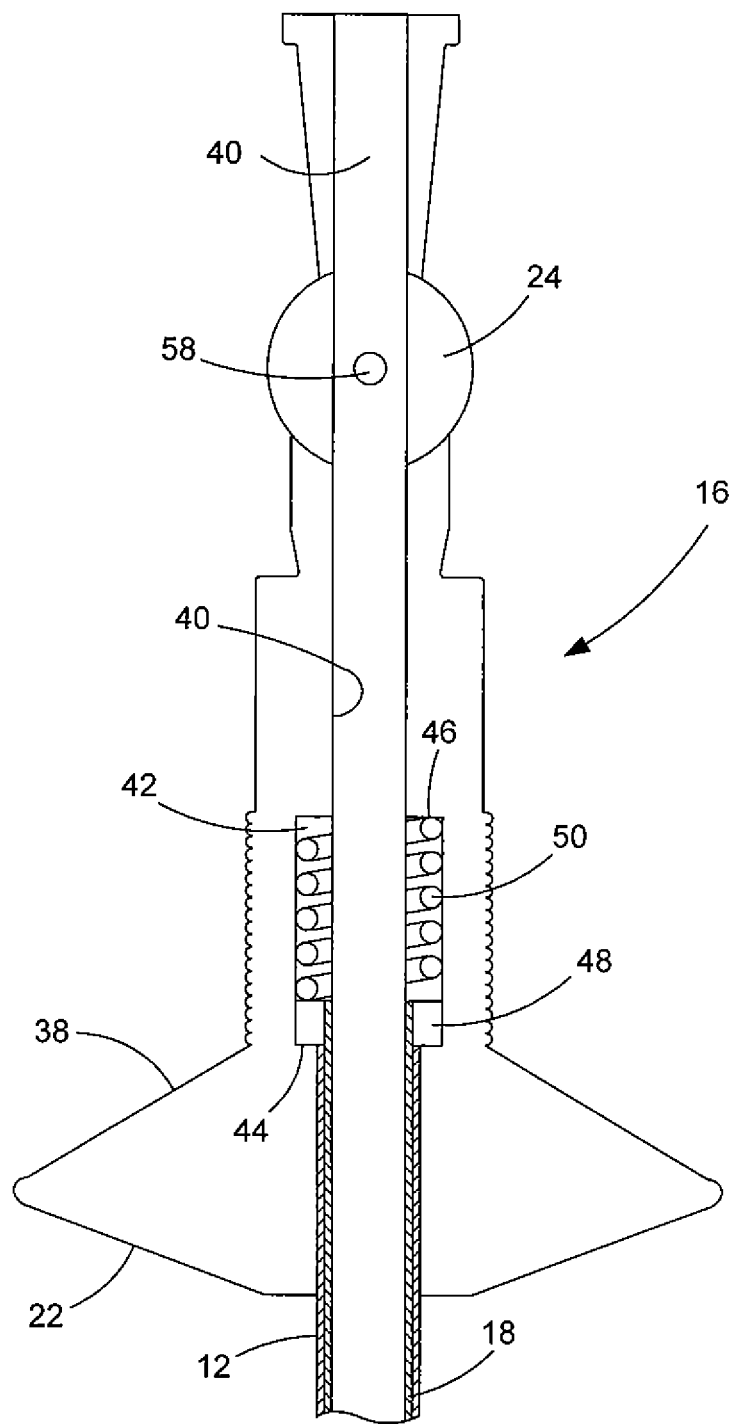
FIG. 6 is a cross-sectional view of an end assembly of the endoscope of FIG. 1, with its image guide removed.

The connector 24 for connecting the insufflation endoscope 10 to a source of insufflation gas provides the connector 24 includes a valve 58 that, when the image guide 30 is removed as shown in FIG. 6, can be operated to allow gas from the gas source to flow into the bore 40. The gas flows from the bore 40 into the hollow interior of the retractable sleeve 18, which is in fluid communication with the bore 40. The gas is then injected into the body cavity through the insufflation channel 28 (as shown in FIG. 4), thereby insufflating the body cavity.

The endoscope 10 can include an optical system for viewing the image produced at the proximal end of the image guide 30. An ocular may be used to magnify the image at the proximal end of the image guide 30. Alternatively, a video relay lens may be used to produce an image directly onto a video camera. It is possible to use an inexpensive CMOS camera, such as those used in cell phone cameras, to produce an image that can be viewed on a video monitor. Further, if a camera is used, a wireless transmitter may be deployed to transfer the image to a remote receiver attached to a video monitor. It is also possible to use the endoscopic camera that will eventually be attached to the general endoscope (such as a laparoscope) to produce the image that can be viewed on the main video monitor or monitors in the operating room. The camera is simply moved from the insufflation endoscope 10 to the general endoscope after the insufflation endoscope 10 is no longer needed for insufflation. A DIN standard eyepiece shape can be used to facilitate the use of the endoscope camera for both applications.

Figure 7:
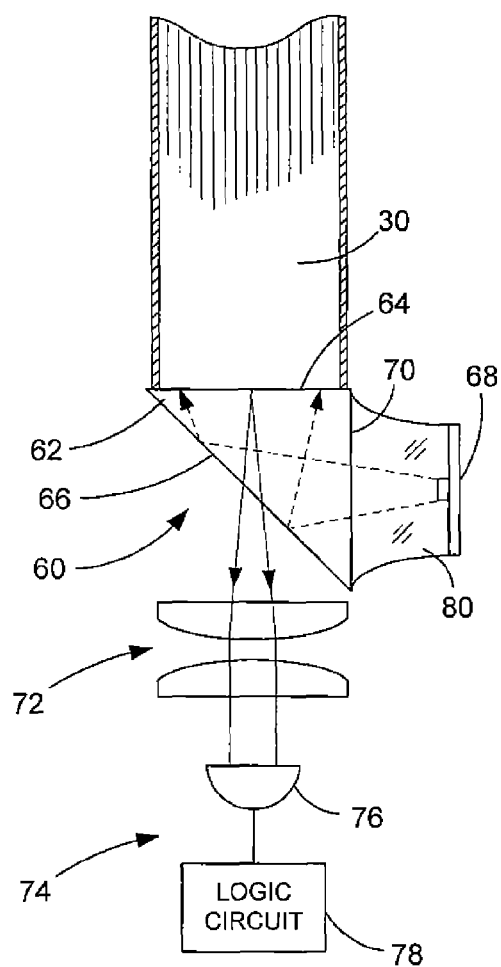
FIG. 7 is a cross-sectional view of an optical system for the endoscope of FIG. 1.

One possible embodiment of an optical system 60 is shown in FIG. 7. The optical system 60 includes a beamsplitter prism 62 having a first surface 64 in contact with the proximal end of the image guide 30 (the knob 52 is not shown in FIG. 7 for convenience). The beamsplitter prism 62 has a second surface 66, ideally disposed at a 45-degree angle to the first surface 64, which is optimally provided with a partially-silvered or partially-aluminized coating having the property wherein some incident light is reflected and some incident light is transmitted. Such coatings are well known in the industry. Additionally, some beamsplitter coatings are designed so that one polarization is reflected from and the other polarization is transmitted through the coating. Such coatings may be more efficient than partially-silvered or partially-aluminized coatings because they absorb less light. These coatings are also well known in the industry.

The optical system 60 further includes a light source 68, such as a light emitting diode (LED) or LED array, located adjacent to the third surface 70 of the beamsplitter prism 62. Light produced by the light source 68 enters the beamsplitter prism 62, and at least some of this light reflects off the second surface 66 and is transmitted through the image guide 30 and the image conduit 20 to illuminate the surface in contact with the distal tip 26. A light trap (not shown) comprising a light absorbing media such as black paint or black velvet is preferably located adjacent to the beamsplitter prism 62, opposite the light source 68. Thus, any light from the light source 68 that is transmitted through the second surface 66 will impinge upon the light trap and be absorbed, thereby reducing glare. An image of the illuminated surface in contact with the distal tip 26 of the image conduit 20 is transmitted back through the image conduit 20 and the image guide 30. This light enters the beamsplitter prism 62 and is at least partially transmitted through the second surface 66. A lens 72 (which can be a compound lens, as shown, or a simple lens, depending on the application) is located adjacent to the third surface 66 to receive light transmitted through the beamsplitter.

As discussed above, the lens 72 could be an ocular, through which a surgeon could view the image of the surface in contact with the distal tip 26, or the lens 72 could be a video relay lens to enable the image to be displayed on a video monitor. In the illustrated embodiment, the lens 72 focuses the image onto a "smart sensor" 74 that automatically detects when the distal tip 26 breaks through the tissue and into the body cavity. When the distal tip 26 breaks through the tissue and into the body cavity, there will be a dramatic change in color and/or intensity of the image being transmitted. By detecting this change in color and/or intensity, the smart sensor 74 is able to determine when the distal tip 26 breaks through the tissue and into the body cavity. The smart sensor 74 can include a light detector 76 which is arranged in line with the lens 72 to receive the image projected through the lens 72. The light detector 76 produces a signal corresponding to the intensity and/or color of the image. The signal produced by the light detector 76 is provided to a logic circuit 78, and when the signal changes dramatically, the logic circuit 78 produces an output signal indicating that the distal tip 26 has broken through the tissue and into the body cavity. It should be noted that the smart sensor 74 could be used in conjunction with either an ocular and/or a video relay lens.

Preferably, the space between the light source 68 and the third surface 70 is filled with an index matching clear adhesive 74 to reduce Fresnel reflections. Thus, all air-to-solid (e.g., air-to-silica or air-to-glass or air-to-plastic) interfaces along the entire optical path (i.e., from the distal tip 26 to the light source 68) are substantially eliminated. Additionally, because the object being viewed is in contact with the distal tip 26, the reflective interface at the tip is also substantially eliminated. Therefore, the endoscope 10 can successfully utilize "through-the-lens" illumination without washing out the image with extraneous reflections. As a possible alternative, illumination may be by conventional optical fibers, as is well known in the art for providing endoscopic illumination. If conventional optical fibers are used, lighting of the field of view is accomplished by transillumination. Transillumination is the scattering of light from the vicinity of the field of view to the actual field of view by scattering within the tissue itself.

When using the endoscope 10, a surgeon is able to visually monitor the making of an initial incision by observing the image output by the optical system 60. This enables the surgeon to precisely and safely position the tip of the endoscope 10 into the body cavity. If it is desired to insufflate the body cavity, the image guide 30 is removed once the tip of the endoscope 10 is properly positioned in the body cavity. The valve 58 is then opened to allow gas from the gas source to flow into the now hollow interior of the endoscope 10 and into the body cavity through the insufflation channel 28 to insufflate the body cavity.

While specific embodiments of the present invention have been described, it should be noted that various modifications thereto could be made without departing from the spirit and scope of the invention as defined in the appended claims.

What is claimed is:
1. An endoscope comprising:
an outer tube having a sharpened distal end;
a retractable sleeve slidably disposed in said outer tube, said retractable sleeve having a sidewall and an insufflation channel formed in said sidewall;
an image guide disposed in said retractable sleeve, said image guide being movable in a sliding manner between an inserted position within said retractable sleeve and a removed position therefrom, said image guide restricting gas flow to said insufflation channel while said image guide is in the inserted position;

a hollow interior formed within said retractable sleeve while said image guide is in the removed position, said hollow interior enabling gas flow to said insufflation channel; and an image conduit fixed in the distal end of said retractable sleeve, the image conduit having a proximal and distal end, wherein the image conduit comprises image fiber having multiple optical fibers fused together with a one-to-one correspondence in the optical fibers' position at the proximal and distal ends of the optical fibers and wherein the image conduit does not function as a lens, and wherein said image conduit transfers an image of an object in contact with a distal tip of the image conduit through said image guide while in the inserted position to the proximal end of said image guide.

2. The endoscope of claim 1 wherein the distal tip of said image conduit extends beyond said distal end of said retractable sleeve.

3. The endoscope of claim 1, wherein the distal end of said image guide is positioned against said image conduit and the proximal end of said image guide extends beyond the proximal end of said retractable sleeve.

4. The endoscope of claim 1 wherein said image fiber is enclosed in a protective sleeve.

5. The endoscope of claim 3 wherein said image guide is removably mounted in said retractable sleeve.

6. The endoscope of claim 3 further comprising an index matching material disposed between said distal end of said image guide and said image conduit.

7. The endoscope of claim 3 further comprising an optical system positioned adjacent to the proximal end of said image guide.

8. The endoscope of claim 7 wherein said optical system includes a beamsplitter in contact with the proximal end of said image guide and a lens located adjacent to said beamsplitter.

9. The endoscope of claim 8 wherein said lens is an ocular.

10. The endoscope of claim 8 wherein said lens is a video relay lens.

11. The endoscope of claim 8 wherein said optical system further includes a light source arranged to direct light into said beamsplitter and then through said image guide.

12. The endoscope of claim 7 wherein said optical system further includes means for determining when said image conduit enters a body cavity.

13. The endoscope of claim 1 further comprising means for connecting the interior of said retractable sleeve to a gas source.

14. The endoscope of claim 13 wherein said insufflation channel is formed adjacent to said image conduit.

15. The endoscope of claim 12 wherein said means for determining includes means for detecting a change in the intensity and/or color of an image transmitted by said image conduit.

16. The endoscope of claim 15 further comprising means for producing an output signal in response to said means for detecting a change in the intensity and/or color of an image transmitted by said image conduit.

17. The endoscope of claim 1 wherein said retractable sleeve is spring-loaded within said outer tube.

18. The endoscope of claim 1, wherein the distal tip of the image conduit has a conical tip for separating soft tissue when making the incision.

19. The endoscope of claim 1, wherein the distal tip of the image conduit has a cutting edge.

20. The endoscope of claim 5, wherein the insufflation channel does not overlap the image conduit.

21. An endoscope comprising:
a sleeve including a proximal and distal end;
an insufflation channel located within said sleeve near said distal end;
an image guide mounted in said sleeve and movable between a first position restricting said insufflation channel from gas flow through said sleeve and a second position allowing gas flow through said sleeve to said insufflation channel;
an image conduit fixed in said distal end of said sleeve, said image conduit transferring, in a return path through said image guide while in said first position, an image of an object in contact with a distal surface of said image conduit to said proximal end while also transmitting light to said distal surface in an initial path opposite to said return path for illumination of said object; and
an index matching material disposed between an interface of said image guide and said image conduit.

22. The endoscope of claim 21 further comprising an optical system including
a beamsplitter in contact with the proximal end of said image guide,
a lens located adjacent to said beamsplitter and oriented in alignment with said return path, and
a light source arranged to direct light into said beamsplitter and then through said image guide.

23. An endoscope comprising:
an outer tube having a sharpened distal end;
a retractable sleeve slidably disposed and spring-loaded within said outer tube, said retractable sleeve including a proximal and distal end;
an insufflation channel located within said retractable sleeve near said distal end;
an image guide mounted in said retractable sleeve and movable between a first position restricting said insufflation channel from gas flow through said retractable sleeve and a second position allowing gas flow through said retractable sleeve to said insufflation channel;
an image conduit fixed to said distal end of said retractable sleeve, said image conduit actuating said retractable sleeve so as to expose said sharpened distal end of said outer tube upon contact of an object with a distal surface of said image conduit, said imagine conduit being fixed in said distal end of said retractable sleeve, said image conduit transferring, in a return path through said image guide, an image of an object in contact with a distal surface of said image conduit to said proximal end while also transmitting light to said distal surface in an initial path opposite to said return path for illumination of said object; and
an index matching material disposed between an interface of said image guide and said image conduit.

\* \* \* \* \*